（12） United States Patent
Kohlmann et al.

(10) Patent No.: US 7,270,143 B2
(45) Date of Patent: Sep. 18, 2007

(54) OFFSET VARIABLE-ORIFICE FLOW SENSOR

(75) Inventors: Thomas Scott Kohlmann, McFarland, WI (US); Lance Clark Bell, Spring Green, WI (US)

(73) Assignee: The General Electric Company, Schenectady, NY (US)

( * ) Notice: Subject to any disclaimer, the term of this patent is extended or adjusted under 35 U.S.C. 154(b) by 118 days.

(21) Appl. No.: 11/304,484

(22) Filed: Dec. 15, 2005

(65) Prior Publication Data

US 2006/0207658 A1 Sep. 21, 2006

Related U.S. Application Data

(63) Continuation-in-part of application No. 11/082,015, filed on Mar. 16, 2005, now abandoned.

(51) Int. Cl.
*F16K 23/00* (2006.01)
*F16K 37/00* (2006.01)
(52) U.S. Cl. .................. 137/312; 137/557; 73/861.53; 138/46
(58) Field of Classification Search ............... 137/312, 137/557; 73/861.53; 138/46
See application file for complete search history.

(56) References Cited

U.S. PATENT DOCUMENTS

| 3,403,556 | A |   | 10/1968 | Koester |   |
|---|---|---|---|---|---|
| 4,083,245 | A |   | 4/1978 | Osborn |   |
| 4,456,016 | A |   | 6/1984 | Nowacki et al. |   |
| 4,989,456 | A |   | 2/1991 | Stupecky |   |
| 5,033,312 | A |   | 7/1991 | Stupecky |   |
| 5,038,621 | A |   | 8/1991 | Stupecky |   |
| 5,970,801 | A | * | 10/1999 | Ciobanu et al. | ......... 73/861.52 |
| 5,979,247 | A |   | 11/1999 | Kizawa |   |
| 6,722,211 | B1 |   | 4/2004 | Ciobanu et al. |   |
| 7,131,451 | B2 | * | 11/2006 | Nugent et al. | ........... 73/861.53 |

* cited by examiner

*Primary Examiner*—Kevin Lee
(74) *Attorney, Agent, or Firm*—Andrus, Sceales, Starke & Sawall, LLP

(57) ABSTRACT

An offset variable orifice gas flow sensor is provided. The variable orifice gas flow sensor comprises two port portions. The central axes of these port portions are offset such that an interior surface of the port portions slope away from a flapper that separates the port portions. The slope ensures that any moisture present in a gas that flows through the variable orifice gas flow sensor drains away from the flapper.

17 Claims, 3 Drawing Sheets

OFFSET VARIABLE-ORIFICE FLOW SENSOR

CROSS REFERENCE TO RELATED APPLICATION

The present application is a continuation-in-part application of U.S. patent application Ser. No. 11/082,015, filed Mar. 16, 2005 and now abandoned.

BACKGROUND OF THE INVENTION

The invention relates generally to flow sensors, and more particularly, to variable orifice flow sensors.

Orifice flow sensors are used to measure the flow rates of fluids, which include liquids and gases. A typical orifice flow sensor comprises a fixed orifice through which a fluid is made to flow. A pressure difference is established between the fluid that is present upstream from the orifice and the fluid that is flowing through the orifice. This pressure difference can be used to measure the flow rate of the fluid. For this purpose, a pressure transducer measures the pressure difference that is established across the orifice, and is calibrated such that the flow rate of the fluid is calculated from this pressure difference.

Variable orifice flow sensors provide sufficient pressure difference for measurement purposes across a broad range of flow rates. This is achieved by introducing a flapper into the fluid flow passage. The flapper bends or flexes in the direction of the fluid flow and hence creates a variable orifice. The measurement of flow rates in a variable orifice flow sensor is similar to the measurement of flow rates in fixed orifice flow sensors. That is, a pressure transducer measures the pressure difference across the variable orifice and calculates the flow rate of the fluid from the pressure difference.

U.S. Pat. Nos. 4,989,456; 5,033,312; 5,038,621; and 6,722,211 show variable orifice flow sensors.

Variable orifice gas flow sensors are commonly used for measuring flow rates in medical applications, such as breathing apparatuses that deliver desired quantities of breathing gases to a patient. When used to measure breathing gases or recirculating breathing gases, the gases flowing through the sensor may contain moisture.

In the case where a gas flowing through a variable orifice flow sensor includes moisture, liquid droplets may accumulate next to the flapper. These liquid droplets restrict the bending of the flapper in the direction of flow of the gas. Therefore, the size of the variable orifice is reduced, and hence, the pressure difference across the variable orifice becomes altered. This leads to inaccurate measurements of the flow rate of the gas.

BRIEF DESCRIPTION OF THE INVENTION

In the present invention a variable orifice gas flow sensor is provided having two port portions that form a gas flow passage through the sensor. A variable orifice means, with a gas flow limiting flapper, is provided between the two port portions. Central axes of the port portions are offset from each other in a direction that is transverse to the flow of a gas through the sensor. The interior surface of at least one of the portions is formed to slope away from the gas flow limiting flapper. The slope ensures that any moisture present in the gas drains away from the gas flow limiting flapper to avoid interfering with the operation of the flapper.

DETAILED DESCRIPTION OF THE INVENTION

Figure 1:
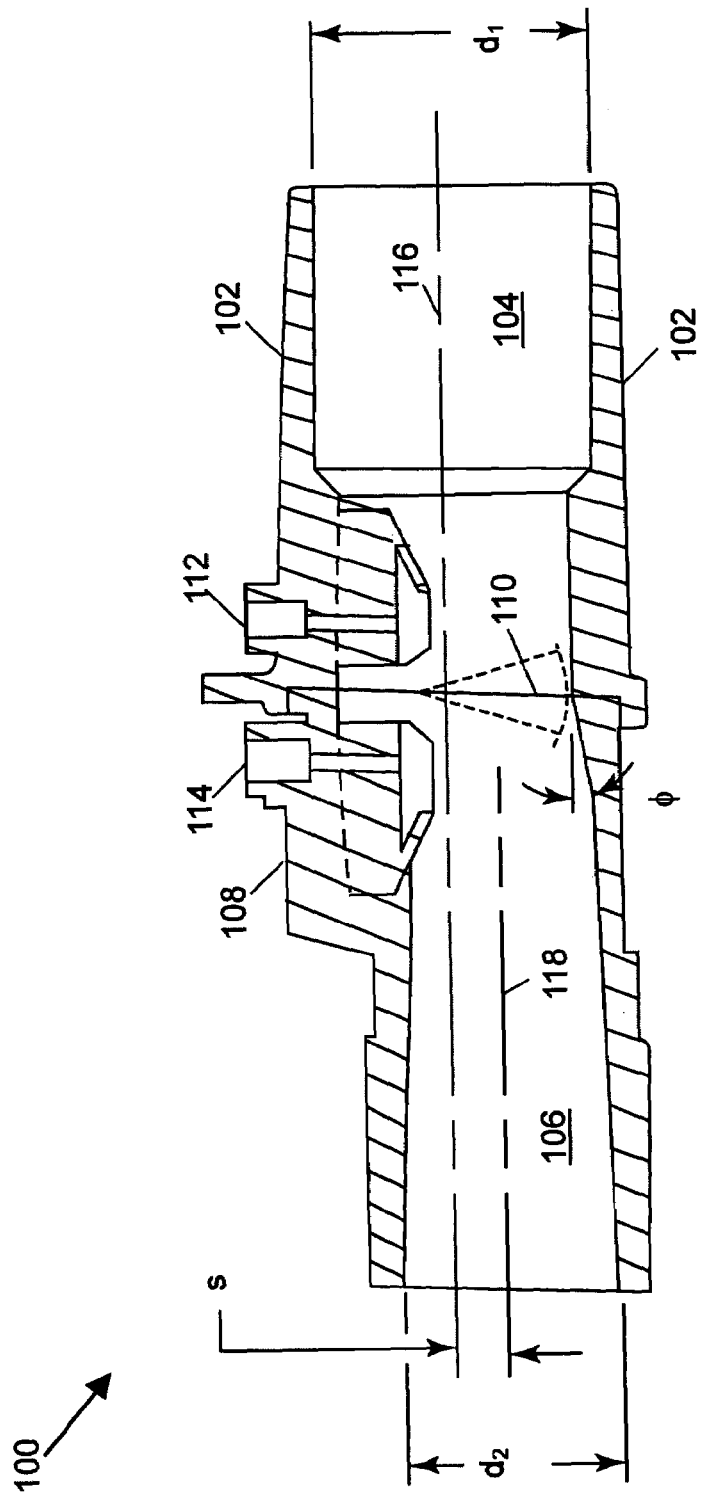
FIG. 1 is a cross sectional view of a variable orifice gas flow sensor in accordance with an exemplary embodiment of the invention.

FIG. 1 illustrates a cross-sectional side view of a variable orifice gas flow sensor 100 in accordance with one embodiment of the present invention. Variable orifice gas flow sensor 100 develops pressure differences that are used to measure flow rates of gases flowing through the flow sensor. Therefore, variable orifice gas flow sensor 100 can also be referred to as a differential pressure gas flow sensor. Variable orifice gas flow sensor 100 has a generally cylindrical configuration. However, variable orifice gas flow sensor 100 may be formed in a variety of shapes and sizes and still lie within the scope of this invention.

Variable orifice gas flow sensor 100 comprises a housing 102 that provides a gas flow passage through which a gas flows. The gas flow passage comprises a first port portion 104 and a second port portion 106 that are separated by a variable orifice means 108. When variable orifice gas flow sensor 100 is used for measuring gas flow rates in a breathing apparatus, a flow sensor 100 is inserted at one or more desired locations in a breathing circuit.

The inner diameter of first port portion 104 is indicated as d1. Similarly, the inner diameter of second port portion 106 is indicated as d2. In an exemplary embodiment of the invention, the value of d1 is taken to be 22 millimeters, and the value of d2 is taken to be 15 millimeters. However, these values are only for exemplary purposes and are not to be construed to be limiting the invention. The diameters d1 and d2 can be chosen depending on the application of variable orifice gas flow sensor 100. The transverse flow areas exhibited by first port portion 104 and second port portion 106 differ. In the example shown in FIG. 1, the transverse flow area of first port portion 104 is greater than the transverse flow area of second port portion 106.

Variable orifice means 108 is intermediate to first port portion 104 and second port portion 106. Variable orifice means 108 has a gas flow limiting flapper 110 that extends into the gas flow passage and separates first port portion 104 and second port portion 106. Gas flow limiting flapper 110 is attached to an inner wall of housing 102. Therefore, as gas flows through variable orifice gas flow sensor 100, gas flow limiting flapper 110 bends or flexes in the direction of the flow of the gas. This bending of gas flow limiting flapper 110 is shown in FIG. 1 in the form of dotted lines. For this purpose, gas flow limiting flapper 110 is made from a resilient material. For example, gas flow limiting flapper 110 can be made from resilient plastic. The bending of gas flow limiting flapper 110 leads to the formation of an increased gas flow opening in the gas flow passage. This gas flow opening varies with the bending of gas flow limiting flapper 110. A pressure difference is established across gas flow limiting flapper 110. This pressure difference is measured by means of a conventional pressure transducer (not shown in FIG. 1). Gas pressures are provided to the pressure transducer through pressure measurement ports 112 and 114, which open into the gas flow passage upstream and downstream of flapper 110. The pressure transducer is calibrated such that the flow rate of the gas, through variable orifice gas flow sensor 100, is obtained from the pressure difference across gas flow limiting flapper 110.

As shown in FIG. 1, a first central axis 116 of first port portion 104 is offset from a second central axis 118 of second port portion 106. This offset is in a direction normal to the direction of the flow of the gas in the gas flow passage (i.e., from left to right or from right to left as shown in FIG. 1) and in the plane of FIG. 1. The extent of this offset is indicated as "s" in FIGS. 1 and 2 and may be 3.5 mm for the diameters d1 and d2 given above. Due to the offset, the portion of the interior surface of the gas flow passage adjacent flapper 110 is established to slope away from gas flow limiting flapper 110 in second port portion 106. The angle of this slope is indicated as φ. The slope provided to the interior surface ensures that any liquid droplets in second port portion 106 do not accumulate near gas flow limiting flapper 110 but are drained away from the flapper. Liquid droplets may be present in variable orifice gas flow sensor 100 due to the presence of moisture in the gas flow. Liquid droplets accumulating next to gas flow limiting flapper 110 restrict the bending of gas flow limiting flapper 110, leading to an alteration in the pressure difference. Hence, the reading of pressure transducer may become altered.

The value of angle φ is chosen such that it is large enough to overcome surface tension of the liquid droplets that accumulate near gas flow limiting flapper 110. For this purpose, the value of angle φ is preferably about 7° of greater. However, if the value of angle φ is too high, then the gas flow in variable orifice flow sensor 100 can become turbulent. This degrades the operation of variable orifice gas flow sensor 100 as the pressure transducer is usually calibrated to give accurate readings for laminar flows. Therefore, the angle should be such that the flow of gas in variable orifice gas flow sensor 100 remains laminar.

Figure 2:
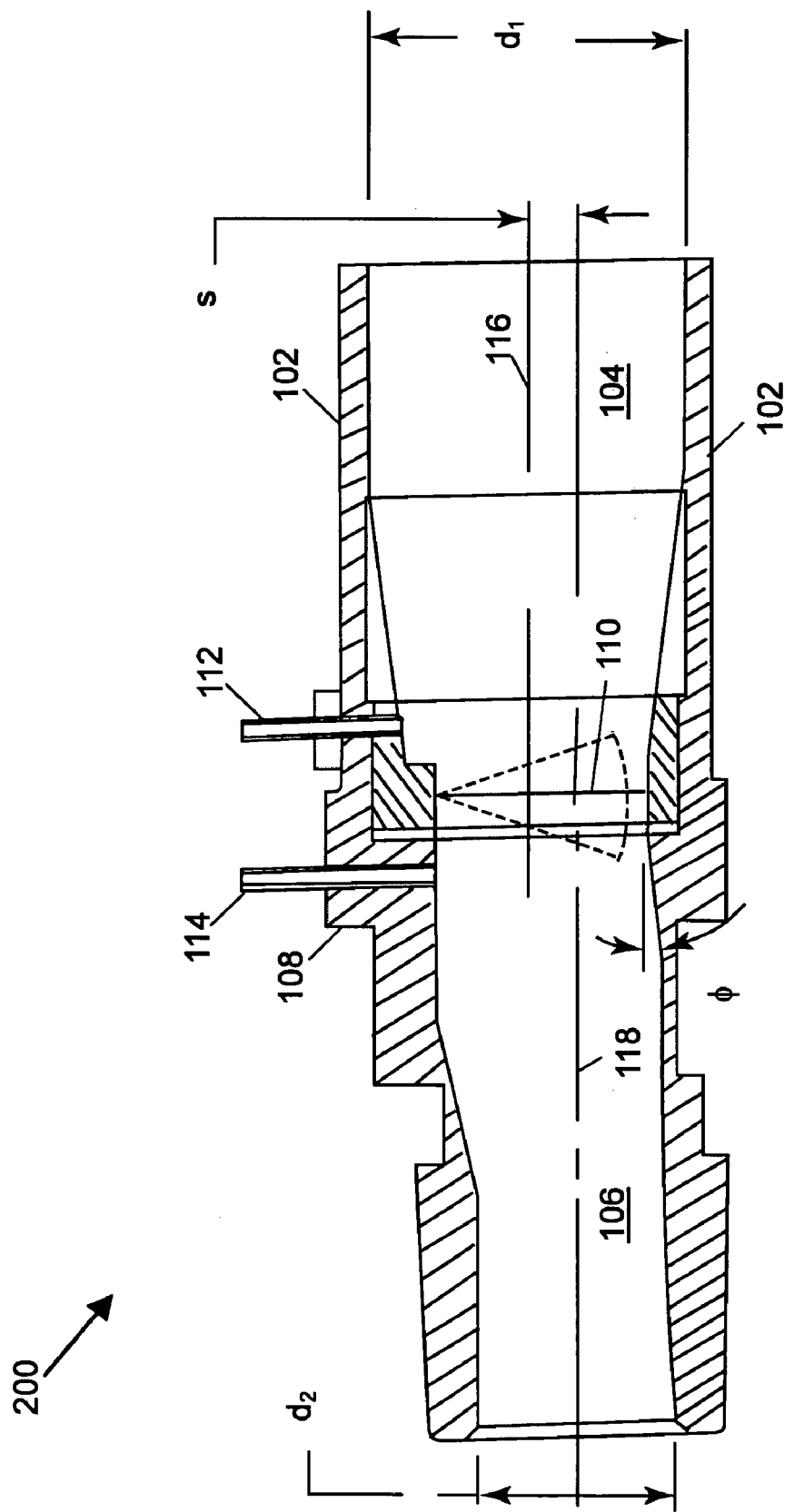
FIG. 2 is a cross sectional view of a variable orifice gas flow sensor in accordance with another exemplary embodiment of the invention.

FIG. 2 illustrates a cross-sectional side view of an variable orifice gas flow sensor 200, in accordance with another embodiment of the present invention in which the interior surface of the gas passage slopes away from gas flow limiting flapper 110 in both directions extending from the flapper.

Figure 3:
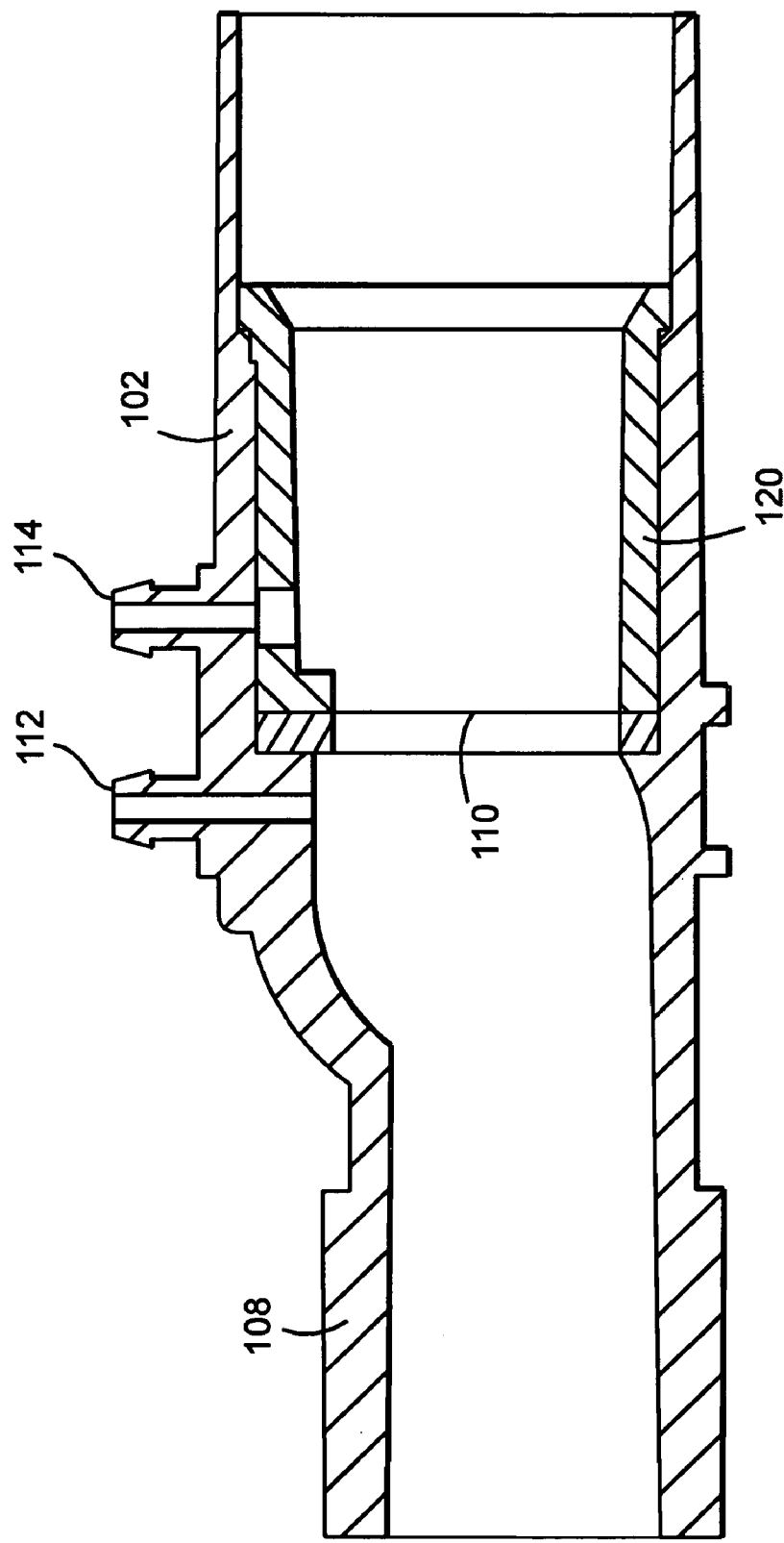
FIG. 3 is a cross sectional view of a variable orifice gas flow sensor in accordance with yet another exemplary embodiment of the invention.

FIG. 3 shows a variable orifice flow sensor 300 in accordance with yet another embodiment of the present invention in which the portions of the interior surface of the gas flow passage adjacent to flapper 110 slope in a curved fashion when the sensor is viewed in cross section, rather than sloping in a linear manner, as shown in FIGS. 1 and 2. For a variable orifice gas flow sensor having the values for dimensions d1 and d2 noted above, the lower interior surface of the gas flow passage may have a radius of curvature of 10 millimeters.

Variable orifice gas flow sensor 100 may be of the single use, disposable type or of the multiple use, reusable type. The former will typically be manufactured from inexpensive plastic material. The latter will usually be manufactured from autoclavable materials, such as metal or high temperature resistant plastic.

Variable orifice gas flow sensor 100 may also include one or more fixed orifices and a flow-limiting member. The fixed orifice ensures that gas flows having a velocity that is insufficient to cause bending of gas flow limiting flapper 110 can pass through variable orifice gas flow sensor 100. This can be achieved by shaping gas flow limiting flapper 110 such that there is space for the gas flow to pass through. A flow limiting member restricts the bending of gas flow limiting flapper 110 to provide an appropriate pressure difference across the flapper for high flow rates.

The various embodiments of the invention provide a variable orifice gas flow sensor that is tolerant to the presence of moisture in gas flows. The variable orifice flow sensor is also able to measure a broad range of flow rates.

While the invention has been described in terms of various specific embodiments, those skilled in the art will recognize that the invention can be practiced with modification within the spirit and scope of the claims.

What is claimed is:

1. A variable orifice gas flow sensor for use with a gas in which moisture may be present, said sensor comprising:
  a housing having a gas flow passage therethrough, said gas flow passage being formed with a first port portion adjacent to one end of said passage and a second port portion adjacent to the other end of said passage, each of said port portions having a central axis, the flow area of one of said port portions transverse to the central axis differing from that of the other of said port portions, the central axis of one of said port portions being offset from the central axis of the other of said port portions in a direction normal to a gas flow direction through said gas flow passage;
  variable orifice means mounted in said gas flow passage intermediate to said first and second port portions, said variable orifice means having a gas flow limiting flapper mounted in an interior surface of said gas flow passage and extending into said gas flow passage for creating a gas flow opening in the passage, the size of said opening being variable responsive to gas flow in said gas flow passage; and
  a portion of said interior surface of said gas flow passage adjacent said variable orifice means being formed to slope away from a central axis of one of said portions in a direction extending away from said flapper to allow moisture from the gas to drain away from said portion of said interior surface adjacent to said variable orifice means.

2. The flow sensor according to claim 1 wherein said interior surface portion slopes away in a direction toward said port portion having the smaller transverse gas flow area.

3. The flow sensor according to claim 1 wherein the sloping of said interior surface portion is in an amount sufficient to overcome surface tension in the moisture.

4. The flow sensor according to claim 1 wherein the sloping of said interior surface portion is in a manner that maintains laminar gas flow in said gas flow passage.

5. The flow sensor according to claim 1 wherein said interior surface portion slopes at an angle of substantially 7 degrees or greater.

6. The flow sensor according to claim 1 wherein the amount of slope of said interior surface portion is determined, at least in part, by the magnitude of the offset of said axes, and wherein the magnitude of said offset is established at an amount to maximize the slope of said interior surface portion yet avoid degradation in the operation of said flow sensor.

7. The flow sensor according to claim 2 wherein the sloping of said interior surface portion is in an amount sufficient to overcome surface tension in the moisture.

8. The flow sensor according to claim 2 wherein the sloping of said interior surface portion is in a manner that maintains laminar gas flow.

9. The flow sensor according to claim 7 wherein said interior surface portion slopes at an angle of substantially 7 degrees or greater.

10. The flow sensor according to claim 2 wherein the amount of slope of said interior surface portion is determined, at least in part, by the magnitude of the offset of axes, and wherein the magnitude of said offset is established at an amount to maximize the slope of said interior surface portion yet avoid degradation in the operation of said flow sensor.

11. The flow sensor according to claim 1 wherein said interior surface portion slopes away in a linear manner.

12. The flow sensor according to claim 1 wherein said interior surface portion slopes away in a curved manner.

13. The flow sensor according to claim 2 wherein said interior surface portion slopes away in a linear manner.

14. The flow sensor according to claim 2 wherein said interior surface portion slopes away in a curved manner.

15. The gas flow sensor according to claim 1 wherein said portion of said interior surface slopes away from a central axis in both directions extending away from said flapper.

16. The flow sensor according to claim 1 further defined as a differential pressure gas flow sensor and wherein said housing has pressure measurement ports opening into said gas flow passage.

17. A variable orifice gas flow sensor for use with a gas in which moisture may be present, said sensor comprising:
a housing having a gas flow passage therethrough, said gas flow passage being formed with a first port portion adjacent to one end of said passage and a second port portion adjacent to the other end of said passage, each of said port portions having a central axis, the flow area of one of said port portions transverse to the central axis differing from that of the other of said port portions, the central axis of one of said port portions being offset from the central axis of the other of said port portions in a direction normal to a gas flow direction through said gas flow passage;
variable orifice means mounted in said gas flow passage intermediate to said first and second port portions, said variable orifice means having a gas flow limiting flapper mounted in an interior surface of said gas flow passage and extending into said gas flow passage for creating a gas flow opening in the passage, the size said opening being variable responsive to gas flow in said gas flow passage; and
a portion of said interior surface of said gas flow passage adjacent said variable orifice means being formed to slope away from a central axis in a direction extending away from said flapper and toward said port portion having the smaller transverse gas flow area, said interior surface portion sloping with respect to said central axis by an amount sufficient to overcome surface tension in the moisture to allow moisture from the gas to drain away from the portion of said interior surface adjacent said variable orifice means.

* * * * *